US00PP14068P39

(12) United States Plant Patent
Asdoorian et al.

(10) Patent No.: US PP14,068 P3
(45) Date of Patent: Aug. 19, 2003

(54) PEACH TREE NAMED 'ISLAND PRINCESS'

(76) Inventors: Alan R. Asdoorian, 522 6th Ave., Kingsburg, CA (US) 93631; Lora A. Asdoorian, 522 6th Ave., Kingsburg, CA (US) 93631

( * ) Notice: Subject to any disclaimer, the term of this patent is extended or adjusted under 35 U.S.C. 154(b) by 0 days.

(21) Appl. No.: 09/895,610

(22) Filed: Jun. 29, 2001

(65) Prior Publication Data

US 2003/0005499 P1 Jan. 2, 2003

(51) Int. Cl.[7] ..... A01H 5/00
(52) U.S. Cl. ..... Plt./197

(58) Field of Search ..... Plt./197

(56) References Cited

U.S. PATENT DOCUMENTS

PP6,025 P 9/1987 Balakian ..... Plt./43.2
PP9,199 P 7/1995 Asdoorian ..... Plt./43.1

*Primary Examiner*—Bruce R. Campell
*Assistant Examiner*—Anne Marie Grünberg

(57) ABSTRACT

A new and distinct variety of peach tree which is somewhat similar to the 'Island King' peach tree (U.S. Plant Pat. No. 9,199) from it is a sport bud from which it is distinguished by producing a later ripening fruit approximately six to eight days after the fruit produced by the 'Island King' peach tree.

1 Drawing Sheet

BACKGROUND OF THE NEW VARIETY

This present invention refers to a new variety of peach which will hereinafter be denominated as the 'Island Princess' peach tree which is a clingstone fruit which is mature for commercial harvesting and shipment May 1–3 in a normal spring year in the San Joaquin Valley of Central California as an early market peach with a good red blush coloration.

In the development of new commercial varieties specific characteristics provide a premium on those fruit varieties which are early or late maturing in the growing season. However, particular early varieties have small size, lack of flavor, or coloration. In some instances there are other undesirable characteristics that decrease the commercial success, such as poor holding or storing capabilities. Therefore, in order for a fruit to be a commercial success, it must be of good size, good color, good flavor, beside good holding capabilities. At the same time the date of maturing must be different from other similar fruit. This new invention meets all of the aforementioned criteria and therefore is of commercial appeal to the consumer.

ORIGIN AND ASEXUAL REPRODUCTION OF THE NEW VARIETY

This present variety was discovered by the inventor in his four acre orchard of 'Island King' peach trees (U.S. Plant Pat. No. 9,199) which is located near Kingsburg, Calif., in the San Joaquin Valley of Central California. The invention was first discovered as a sport of the 'Island King' tree in 1998. The new variety was first asexually reproduced in the dormant season of 1999/2000 by bud grafting onto 600 Nemaguard Rootstocks on the owner's property, adjacent to the original peach orchard. The asexually reproduced trees first bore fruit of the new variety in May 2001. The inventory carefully compared the asexually reproduced trees with the parent sport, including the fruit and the parent, and the progeny are in all respects identical to the parent tree.

SUMMARY OF THE NEW VARIETY

The 'Island Princess' Peach tree is characterized by producing a large clingstone fruit which has good blush coloration and is ripe for commercial harvesting and shipment approximately May 1–3 in the San Joaquin Valley of Central California. The new variety is most similar to 'Island King' peach tree (U.S. Plant Pat. No. 9,199) from which it is a sport but from which it is distinguishable in that it ripens six to eight days later than the fruit of the 'Island King' peach tree and 4–6 days before 'Island Prince' (U.S. Plant Pat. No. 12,102). The fruit of this new variety possesses a very good flavor with a pleasant aroma which makes it greatly acceptable for an early ripening variety.

BRIEF DESCRIPTION OF THE DRAWING

The accompanying drawing is a color photograph displaying fruit, foliage, and a piece of second year branch at the top of the photograph. Foliage of the upper side of the leaves are on the left side of the photograph while foliage of the underside of the leaves are on the right side; four whole fruit are in the center with the upper left displaying the suture, the upper right displaying the blossom end of the fruit, the lower left fruit shows a side view with the cheek surface and the lower right the distal end of the fruit. At the bottom a fruit is cut in half with the left side showing the flesh and pit well, a pit in the center with a half of the fruit showing the flesh and pit.

DETAILED DESCRIPTION

Referring more specifically to the pomological description of this new and distinct variety of peach tree, the following details have been observed under the ecological conditions prevailing in the orchard of origin which is located near Kingsburg, Calif. the San Joaquin Valley of Central California. All major color code designations are by reference to Dictionary of Color by Maerz and Paul, First Edition, 1930. Common color names are also occasionally employed.

Tree

Size: Small to medium in height and width — 4–5 ft. in height, 3 ft. spread.
Vigor: Early indicates that vigor is good (40–49 inches of new growth this growing season.)
Figure (form): Open and spreading with open vase system of training. Productivity is good for tree of this age. Normal regular bearing (i.e., every year, not in alternate years).
Trunk size: At level above the graft union, approximately 10–12" above soil level. Circumference is 1.875 inch 42.61mm.
Color: Beaver (15-A-6).
Branches:
*Size.*—Medium.
*Circumference.*—1.0625 inches (16.74–26.99 mm).
*a. Mature.*—Slightly rough.
*b. Immature.*—Smooth.
*Color code* (*one year or older*).—Horse chestnut (8-J-5).
*Color code* (*immature*).—Near Calliste green (19-L-7).

Three to four scaffold with lateral branches, at this stage of growth, developing fruitwood and allow sunlight for fruit colors.

Leaves

Size: Medium to large.
Length: 135 mm–151 mm(5.31–5.94 inches).
Width: 32 mm–38 mm (1.26–1.50 inches).
Color code:
*Upper surface.*—Mt. Vernon Green (23-J-8).
*Lower surface.*—Art Green (22-L-7).
Margin form: Crenate.
Leaf vein:
*Color code.*—*Shadow Green (*20-J-3).
*Thickness.*—1 mm.
Glandular characteristics: Reniform — 2 — opposite sides of leaf at the base.
Petiole:
*Size.*—Medium.
*Length.*—10 mm–12 mm (0.37–0.37 inch).
*Diameter.*—2 mm (0.8 inch).
*Color code.*—Shadow green (20-J-3).

Flowers

Flower buds: Hardy under typical San Joaquin Valley, Central California climate conditions.
*Size.*—Medium.
*Diameter*—6 mm (0.24 inch).
*Length.*—10 mm (0.41 inch).
*Form.*—Conic shape.
Bud scales:
Color: Maroon near sepals (7-L-7).
Generally: Showy type.
Date of bloom: Approximately 15–20% by Feb. 28, 2001 with full bloom by March 10th.
Size of flowers: Medium to large.
Diameter — when fully expanded: 43 mm–45 mm (1.67–1.77 inches).
Bloom quality: Abundant.
Petals:
*Size.*—Medium to large.
*Length.*—16–18 mm.
*Width.*—15–18 mm.
*Form.*—Broadly ovate.
*Number.*—6.
Color: Pink (1-D- 1).
Petal claws: Broadly truncate.
*Width.*—1 mm (0.04 inch).
*Length.*—1.5 mm (0.59 inch).
Petal margins: Moderately undulated with rounded edges.
Flower pedicel: very short Avg 2 mm (0.8 inch).
*Color.*—Lily Green (19-A-5).
*Surface.*—Pubescent.
Sepals:
*Size.*—Medium to large, 6.3 mm (0.25 inch).
*Color.*—Amaranth (44-L-1).
*Number.*—5.
Anthers:
*Size.*—Small.
*Color.*—Mineral R (6-J-3). Center is Straw (10-F-2).
Stamens: 10–18 mm (0.39–0.71 inch).
*Filament color.*—Very Light Pink (1-B-1).
*Number.*—35–45.
Pistil:
*Length.*—18 mm (0.71 inch).
*Color.*—Absinthe green (20-J-5).
Surface: Pubescent.
Number: One.

Fruit

Date of maturity: May 1–3 in the San Joaquin Valley of Central California.
Size:
*Diameter axial plane.*—58 mm–64 mm (2.28–2.54 inch).
*Transverse in suture plane.*—60 mm–66 mm (2.36 inch–2.60 inch).
*Transverse at rt. angle to suture plane.*—62 mm–65 mm (2.44 inch–2.68 inch).
Form: Uniform. Symmetrical or Asymmetrical — Shape of fruit is slightly asymmetrical.
Suture: Shallow with Yellow coloration from stem end to apex.
*Ventral surface:* Uneven.
Stem cavity:
*Width.*—20 mm (0.79 inch).
*Depth.*—12 mm (0.47 inch).
*Length.*—21 mm (0.83 inch).
Stem: Short.
*Diameter.*—10 mm–12 mm (0.39 inch–0.47 inch).
*Caliper.*—6 mm–8 (0.24–0.31 ).
Apex: Slightly rounded.
Pistil point: Oblique.
Skin: Thickness normal for peach, slightly pubescent.
Texture: Firm.
Tendency to crack: None observed.
Color code:
*Blush color.*—Chalet R (6-K-10) — over 50% of fruit.
*Ground color.*—Corn (10-J-5).
*Flesh color.*—Apricot Y (9-K-5) .
*Color of surface of pit cavity.*—Apricot (9-K-5).
*Color of pit well.*—Apricot (9-K-5).
Juice production: Moderate.
Aroma: Good.
Texture: Firm.
Fibers:
*New.*—Few.
*Texture.*—Firm.
Ripening: Even.
Eating quality: Very good.

Stone:

*Attachment.*—Clingstone.

*Fibers.*—Few, moderate in length.

*Size.*—Length — 3 mm–38 mm (1.29–1.50 inch). Width — 23 mm–26mm (0.91–1.02 inch). Thickness — 16 mm–21 mm (0.63–0.83 inch).

Form: Ovate.

Apex: Sharply acute.

Color Code, when dry: Toast (13-E-8).

Base: Somewhat ovate in shape.

Sides: Unequal.

Ridges: On both sides of stone with narrow ridge on ventral sides.

Tendency to split: None observed.

Use: Fresh Market.

The above description of this new variety of peach tree is based on growing conditions prevailing near Kingsburg, Calif. in the Central San Joaquin Valley of California. Variations of the usual magnitude and characteristics may occur due to changes in cultural practices including irrigation, fertilization, pruning practices, and changes in the weather conditions.

A new and distinct variety of peach tree as described and illustrated which is somewhat similar to 'Island King' (U.S. Plant Pat. No. 9,199) from it is a bud sport but from which it is distinguished by producing fruit that ripens 6–8 days after 'Island King' and 4–6 days before 'Island Prince' (U.S. Plant Pat. No. 12,102) with good exterior color and eating quality which mature for harvesting and commercial shipment May 1–3 in a normal year.

We claim:

1. A new and distinct variety of peach tree as described and illustrated which is somewhat similar to 'Island King' (U.S. Plant Pat. No. 9,199) from which it is a bud sport but from which it is distinguished by producing fruit that ripens 6–8 days after 'Island King' with good exterior color and eating quality which are mature for commercial harvesting and shipment approximately May 1 to 3 in a normal year.

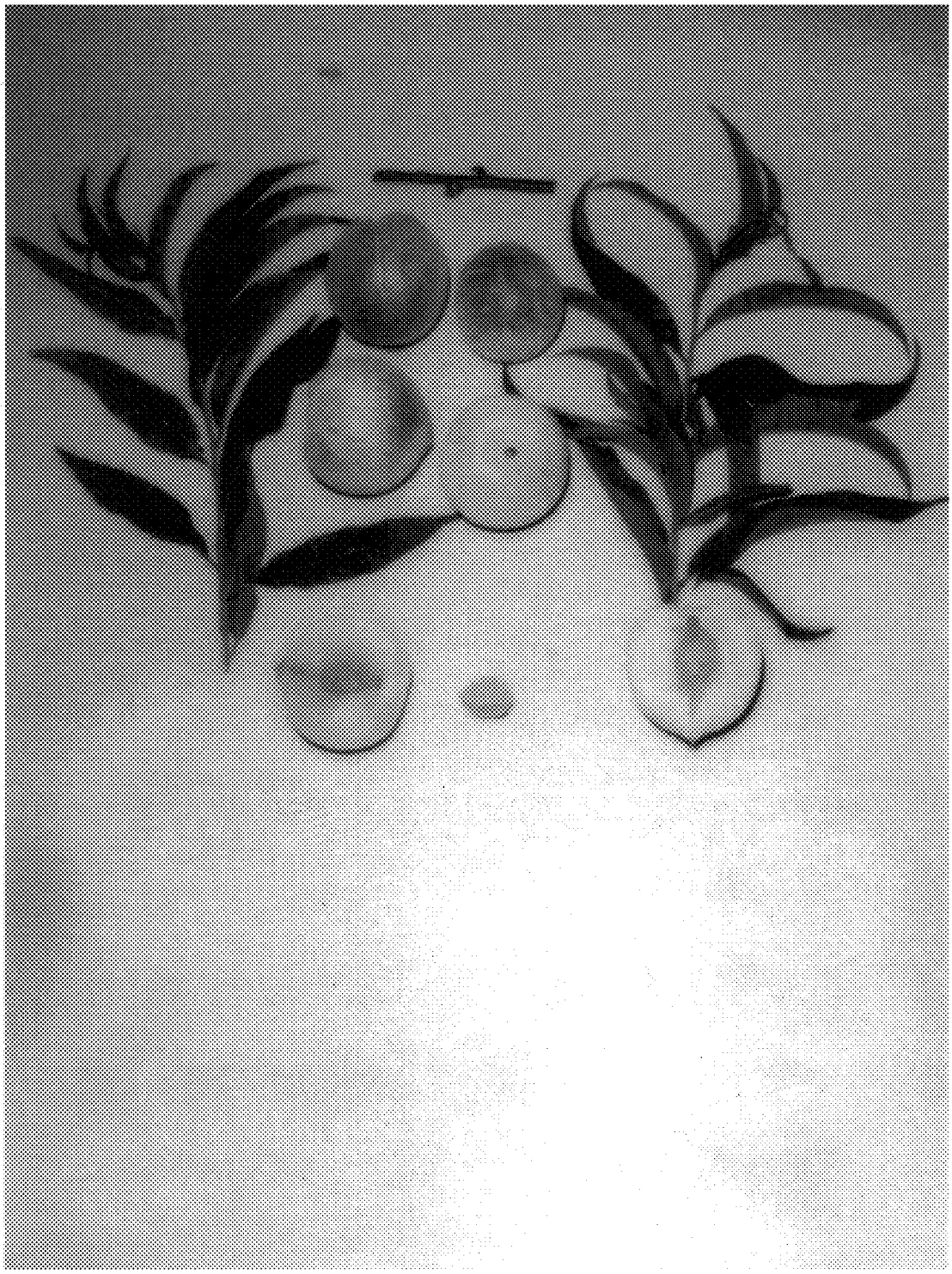

* * * * *